(12) United States Patent
Matsumura et al.

(10) Patent No.: US 7,437,189 B2
(45) Date of Patent: Oct. 14, 2008

(54) IONTOPHORESIS DEVICE

(75) Inventors: Akihiko Matsumura, Shibuya-ku (JP);
Takehiko Matsumura, Shibuya-ku (JP);
Mizuo Nakayama, Shibuya-ku (JP);
Hidero Akiyama, Shibuya-ku (JP);
Tsutomu Shibata, Shibuya-ku (JP);
Akihiko Tanioka, Ohota-ku (JP)

(73) Assignee: TTI ellebeau, Inc., Tokyo (JP)

( * ) Notice: Subject to any disclaimer, the term of this patent is extended or adjusted under 35 U.S.C. 154(b) by 0 days.

(21) Appl. No.: 11/196,783

(22) Filed: Aug. 2, 2005

(65) Prior Publication Data

US 2006/0217654 A1      Sep. 28, 2006

(30) Foreign Application Priority Data

Mar. 22, 2005   (JP)   ............... 2005-081220

(51) Int. Cl.
*A61N 1/30*   (2006.01)
*A61M 5/32*   (2006.01)

(52) U.S. Cl. ..................... 604/21; 604/272

(58) Field of Classification Search ........... 604/501, 604/20–22, 264, 272–274, 93.01
See application file for complete search history.

(56) References Cited

U.S. PATENT DOCUMENTS

| | | | |
|---|---|---|---|
| 3,964,482 A * | 6/1976 | Gerstel et al. ............. | 604/890.1 |
| 4,519,938 A | 5/1985 | Papir ......................... | 252/500 |
| 4,722,726 A | 2/1988 | Sanderson et al. ............ | 604/20 |
| 4,731,049 A | 3/1988 | Parsi ........................... | 604/20 |
| 4,744,787 A | 5/1988 | Phipps et al. ............... | 604/20 |
| 4,747,819 A | 5/1988 | Phipps et al. ............... | 604/20 |
| 4,915,685 A | 4/1990 | Petelenz et al. ............. | 604/20 |
| 5,057,072 A | 10/1991 | Phipps ........................ | 604/20 |
| 5,080,646 A | 1/1992 | Theeuwes et al. ............ | 604/20 |
| 5,084,006 A | 1/1992 | Lew et al. .................... | 604/20 |
| 5,084,008 A | 1/1992 | Phipps ........................ | 604/20 |
| 5,135,477 A | 8/1992 | Untereker et al. ............ | 604/20 |
| 5,147,296 A | 9/1992 | Theeuwes et al. ............ | 604/20 |

(Continued)

FOREIGN PATENT DOCUMENTS

CA       2205444       6/1996

(Continued)

OTHER PUBLICATIONS

Amer, S., et al., "An Integrated Platform for Bio-analysis and Drug Delivery," *Curr Pharm Biotechnol.*, 6(1):57-64, Feb. 2005.

(Continued)

*Primary Examiner*—Matthew F DeSanto
(74) *Attorney, Agent, or Firm*—Seed IP Law Group PLLC

(57) ABSTRACT

An iontophoresis device includes: a first electrode; a biological interface contact member including a substrate having a front surface and a rear surface, and a plurality of needles that protrude from the front surface of the substrate and can be inserted into a biological interface, the biological interface contact member allowing selective permeation of ions of a first polarity; and a drug holding part applied with an electrical potential or voltage through the first electrode and holding a drug solution containing drug ions charged in the first polarity, the drug holding part being interposed between the first electrode and the biological interface contact member.

10 Claims, 5 Drawing Sheets

U.S. PATENT DOCUMENTS

| | | | |
|---|---|---|---|
| 5,162,043 A | 11/1992 | Lew et al. | 604/20 |
| 5,169,383 A | 12/1992 | Gyory et al. | 604/20 |
| 5,238,613 A | 8/1993 | Anderson | 264/22 |
| 5,322,502 A | 6/1994 | Theeuwes et al. | 604/20 |
| 5,326,341 A | 7/1994 | Lew et al. | 604/20 |
| 5,395,310 A | 3/1995 | Untereker et al. | 604/20 |
| 5,405,317 A | 4/1995 | Myers et al. | 604/20 |
| 5,496,266 A | 3/1996 | Haak et al. | 604/20 |
| 5,503,632 A | 4/1996 | Haak | 604/20 |
| 5,543,098 A | 8/1996 | Myers et al. | 264/104 |
| 5,573,668 A | 11/1996 | Grosh et al. | 210/490 |
| 5,637,084 A | 6/1997 | Kontturi et al. | 604/20 |
| 5,647,844 A | 7/1997 | Haak et al. | 604/20 |
| 5,668,170 A | 9/1997 | Gyory | 514/449 |
| 5,711,761 A | 1/1998 | Untereker et al. | 604/20 |
| 5,788,666 A | 8/1998 | Atanasoska | 604/20 |
| 5,840,056 A | 11/1998 | Atanasoska | 604/20 |
| 5,871,460 A | 2/1999 | Phipps et al. | 604/20 |
| 5,941,843 A | 8/1999 | Atanasoska et al. | 604/20 |
| 5,993,435 A * | 11/1999 | Haak et al. | 604/501 |
| 6,049,733 A | 4/2000 | Phipps et al. | 604/20 |
| 6,064,908 A | 5/2000 | Muller et al. | 604/20 |
| 6,103,078 A | 8/2000 | Hitchems et al. | 204/296 |
| 6,109,852 A | 8/2000 | Shahinpoor et al. | 414/1 |
| 6,132,755 A | 10/2000 | Eicher et al. | 424/427 |
| 6,169,920 B1 | 1/2001 | Haak et al. | 604/20 |
| 6,185,453 B1 * | 2/2001 | Hussain et al. | 604/21 |
| 6,219,574 B1 * | 4/2001 | Cormier et al. | 604/20 |
| 6,256,533 B1 | 7/2001 | Yuzhakov et al. | 604/21 |
| 6,258,276 B1 | 7/2001 | Mika et al. | 210/638 |
| 6,312,612 B1 | 11/2001 | Sherman et al. | 216/2 |
| 6,314,317 B1 | 11/2001 | Willis | 604/20 |
| 6,329,488 B1 | 12/2001 | Terry et al. | 528/28 |
| 6,334,856 B1 | 1/2002 | Allen et al. | 604/191 |
| 6,350,259 B1 | 2/2002 | Sage, Jr. et al. | 604/501 |
| 6,377,847 B1 | 4/2002 | Keusch et al. | 604/20 |
| 6,377,848 B1 | 4/2002 | Garde et al. | 604/20 |
| 6,379,324 B1 | 4/2002 | Gartstein et al. | 604/22 |
| 6,385,488 B1 | 5/2002 | Flower et al. | 604/20 |
| 6,394,994 B1 | 5/2002 | Vilambi et al. | 604/501 |
| 6,402,732 B1 | 6/2002 | Flower et al. | 604/501 |
| 6,405,875 B1 * | 6/2002 | Cutler | 210/477 |
| 6,406,638 B1 | 6/2002 | Stoeber et al. | 216/11 |
| 6,451,240 B1 | 9/2002 | Sherman et al. | 264/504 |
| 6,454,941 B1 * | 9/2002 | Cutler et al. | 210/266 |
| 6,462,935 B1 * | 10/2002 | Shiue et al. | 361/511 |
| 6,471,903 B2 | 10/2002 | Sherman et al. | 264/328.1 |
| 6,497,887 B1 | 12/2002 | Zecchino et al. | 424/401 |
| 6,503,231 B1 | 1/2003 | Prausnitz et al. | 604/272 |
| 6,511,463 B1 | 1/2003 | Wood et al. | 604/272 |
| 6,522,919 B1 | 2/2003 | Flower et al. | 604/20 |
| 6,533,949 B1 | 3/2003 | Yeshurun et al. | 216/11 |
| 6,553,255 B1 | 4/2003 | Miller et al. | 604/20 |
| 6,565,532 B1 | 5/2003 | Yuzhakov et al. | 604/142 |
| 6,584,349 B1 | 6/2003 | Sage, Jr. et al. | 604/20 |
| 6,596,401 B1 | 7/2003 | Terry et al. | 428/447 |
| 6,603,987 B2 | 8/2003 | Whitson | 600/345 |
| 6,603,998 B1 | 8/2003 | King et al. | 604/20 |
| 6,611,707 B1 | 8/2003 | Prausnitz et al. | 604/21 |
| 6,629,968 B1 | 10/2003 | Jain et al. | 604/501 |
| 6,635,045 B2 | 10/2003 | Keusch et al. | 604/20 |
| 6,663,820 B2 | 12/2003 | Arias et al. | 264/496 |
| 6,678,554 B1 * | 1/2004 | Sun et al. | 604/20 |
| 6,678,555 B2 | 1/2004 | Flower et al. | 604/20 |
| 6,767,341 B2 | 7/2004 | Cho | 604/272 |
| 6,790,372 B2 | 9/2004 | Roy et al. | 216/10 |
| 6,815,360 B1 | 11/2004 | Canham et al. | 438/706 |
| 6,844,028 B2 | 1/2005 | Mao et al. | 427/384 |
| 6,846,681 B2 | 1/2005 | Buriak et al. | 436/527 |
| 6,858,018 B1 | 2/2005 | Green et al. | 604/19 |
| 6,862,473 B2 | 3/2005 | Keusch et al. | 604/20 |
| 6,881,203 B2 | 4/2005 | Delmore et al. | 604/272 |
| 6,908,453 B2 | 6/2005 | Fleming et al. | 604/173 |
| 6,908,681 B2 | 6/2005 | Terry et al. | 428/447 |
| 6,918,901 B1 | 7/2005 | Theeuwes et al. | 604/500 |
| 6,939,311 B2 | 9/2005 | Geiger | 600/573 |
| 6,980,855 B2 | 12/2005 | Cho | 604/20 |
| 7,018,345 B2 * | 3/2006 | Mori et al. | 600/573 |
| 7,018,370 B2 * | 3/2006 | Southam et al. | 604/501 |
| 7,184,826 B2 | 2/2007 | Cormier et al. | 604/21 |
| 2002/0016562 A1 | 2/2002 | Cormier et al. | 604/20 |
| 2002/0022795 A1 | 2/2002 | Reynolds et al. | 604/20 |
| 2002/0099320 A1 | 7/2002 | Beck | 604/20 |
| 2002/0133129 A1 | 9/2002 | Arias et al. | 604/272 |
| 2002/0193754 A1 | 12/2002 | Cho | 604/272 |
| 2003/0065305 A1 | 4/2003 | Higuchi et al. | 604/501 |
| 2003/0168404 A1 | 9/2003 | Mika et al. | 210/639 |
| 2004/0105881 A1 | 6/2004 | Cevc et al. | 424/450 |
| 2004/0167459 A1 | 8/2004 | Higuchi et al. | 604/20 |
| 2005/0011826 A1 | 1/2005 | Childs et al. | 210/490 |
| 2005/0070840 A1 | 3/2005 | Matsumura et al. | 604/20 |
| 2006/0074377 A1 | 4/2006 | Cormier et al. | 604/47 |
| 2006/0095001 A1 | 5/2006 | Matsumura et al. | 604/20 |
| 2006/0116628 A1 | 6/2006 | Matsumura et al. | 604/20 |
| 2006/0129085 A1 | 6/2006 | Tanioka et al. | 604/20 |
| 2006/0135906 A1 | 6/2006 | Matsumura et al. | 604/20 |
| 2006/0173401 A1 | 8/2006 | Tanioka et al. | 604/20 |
| 2006/0211980 A1 | 9/2006 | Cormier et al. | 604/20 |
| 2006/0217654 A1 | 9/2006 | Matsumura et al. | 604/20 |
| 2006/0276742 A1 | 12/2006 | Matsumura et al. | 604/20 |
| 2007/0021711 A1 | 1/2007 | Matsumura et al. | 604/20 |
| 2007/0027426 A1 | 2/2007 | Matsumura et al. | 604/20 |
| 2007/0060859 A1 | 3/2007 | Kanamura et al. | 604/20 |
| 2007/0060860 A1 | 3/2007 | Nakayama et al. | 604/20 |
| 2007/0066930 A1 | 3/2007 | Tanioka et al. | 604/20 |
| 2007/0066931 A1 | 3/2007 | Kanamura et al. | 604/20 |
| 2007/0071807 A1 | 3/2007 | Akiyama et al. | 424/451 |
| 2007/0073212 A1 | 3/2007 | Matsumura | 604/20 |
| 2007/0078375 A1 | 4/2007 | Smith | 604/20 |
| 2007/0078376 A1 | 4/2007 | Smith | 604/21 |
| 2007/0083147 A1 | 4/2007 | Smith | 604/20 |
| 2007/0083185 A1 | 4/2007 | Carter | 604/501 |
| 2007/0088332 A1 | 4/2007 | Akiyama et al. | 604/890.1 |
| 2007/0093787 A1 | 4/2007 | Smith | 604/890.1 |
| 2007/0112294 A1 | 5/2007 | Akiyama et al. | 604/20 |
| 2007/0135754 A1 | 6/2007 | Akiyama et al. | 604/20 |
| 2007/0197955 A1 | 8/2007 | Akiyama et al. | 604/20 |
| 2007/0213652 A1 | 9/2007 | Carter | 604/20 |

FOREIGN PATENT DOCUMENTS

| | | |
|---|---|---|
| GB | 2 265 088 A | 9/1993 |
| JP | 52-151720 | 12/1977 |
| JP | 60-35936 | 2/1985 |
| JP | 3-94771 | 4/1991 |
| JP | 3-504343 | 9/1991 |
| JP | 04-297277 | 10/1992 |
| JP | 5220385 | 8/1993 |
| JP | 08-164212 | 6/1996 |
| JP | 09-201420 | 8/1997 |
| JP | 10-510175 | 10/1998 |
| JP | 2845509 | 10/1998 |
| JP | 2000-229128 | 8/2000 |
| JP | 2000-229129 | 8/2000 |
| JP | 2000-237326 | 9/2000 |
| JP | 2000-237327 | 9/2000 |
| JP | 2000-237328 | 9/2000 |
| JP | 2000-237329 | 9/2000 |
| JP | 2000-288097 | 10/2000 |
| JP | 2000-288098 | 10/2000 |
| JP | 2002-233584 | 8/2002 |
| JP | 2002-535100 | 10/2002 |
| JP | 2004-188188 | 7/2004 |
| JP | 2004-202057 | 7/2004 |

| | | |
|---|---|---|
| JP | 2004-292438 | 10/2004 |
| JP | 2004-317317 | 10/2004 |
| JP | 2004-357313 | 12/2004 |
| JP | 2005-503194 | 2/2005 |
| JP | 2006-149891 | 6/2006 |
| JP | 2006-212194 | 8/2006 |
| JP | 2006-262943 | 10/2006 |
| JP | 2007-037640 | 2/2007 |
| JP | 2007-050136 | 3/2007 |
| WO | WO 90/03825 | 4/1990 |
| WO | WO 90/04433 | 5/1990 |
| WO | WO 90/08571 | 8/1990 |
| WO | WO 91/16943 | 11/1991 |
| WO | WO 93/17754 | 9/1993 |
| WO | WO96/17648 | 6/1996 |
| WO | WO 97/47353 | 12/1997 |
| WO | WO 99/22655 | 5/1999 |
| WO | WO 00/44438 | 8/2000 |
| WO | WO 02/07813 | 1/2002 |
| WO | WO 02/072189 | 9/2002 |
| WO | WO02/100474 | 12/2002 |
| WO | WO 03/008078 | 1/2003 |
| WO | WO03/037425 | 5/2003 |
| WO | WO 03/047689 | 6/2003 |
| WO | WO 2004/073843 | 9/2004 |
| WO | WO 2006/062108 | 6/2006 |

OTHER PUBLICATIONS

Dow Corning, "A Guide to Silane Solutions from Dow Corning," URL: http://www.dowcorning.com/content/publishedlit/SILANE-GUIDE.pdf.

Fu, W., et. al., "Biomedical Applications of Gold Nanoparticles Functionalized Using Hetero-Bifunctional Poly(ethyleneglycol) Spacer," *Mater. Res. Soc. Symp. Proc. 845*, AA5.4.1, 2005.

Ito, Y., et al. "In vitro Effect of Ion Exchange Membrane on Iontophoresis," *Medicine and Biology*, 147(3):41-46, 2003.

JIS (Japanese Industrial Standards), "Testing Methods for Bubble Point of Membrane Filters," K3832-1990.

Martanto, W., et al., "Side-opening Hollow Microneedles for Transdermal Drug Delivery," in Proceedings of the *32nd Annual Meeting of the Controlled Release Society*, Florida, Jun. 2005, 2 pages.

Naoya Ogata, "Dodensei Kobunshi" (Electrically Conductive High Molecular Compounds), Kodansha Scientific, (1990).

Prausnitz, M., "Microneedles for Transdermal Drug Delivery," *Adv Drug Deliv Rev.*, 56(5):581-7, Mar. 27, 2004.

Rodriguez, A., "Fabrication of Silicon Oxide Microneedles from Macroporous Silicon," in *Proceedings of the European Materials Conference*, Poland, Sep. 6-10, 2004, p. 38.

Wilke, N., et al., "Silicon Microneedle Formation Using Modified Mask Designs Based on Convex Corner Undercut," URL: http://www.nicolle-wilke.de/documents/MST_kongress_05.pdf.

Xie, Y., et al., "Controlled Transdermal Delivery of Model Drug Compounds by MEMS Microneedle Array," *Nanomedicine*, 1(2):184-90, Jun. 2005.

* cited by examiner

US 7,437,189 B2

IONTOPHORESIS DEVICE

BACKGROUND OF THE INVENTION

1. Field of the Invention

The present disclosure relates to an iontophoresis device for applying an electrical field to a drug dissociated into cations or anions in a solution to thereby percutaneously drive the ions (anions and cations) to a living body.

2. Description of the Related Art

Iontophoresis is a technique of applying an electric field to a drug dissociated into cations or anions in a solution to thereby allow the ions (anions and cations) to percutaneously transfer into a living body. This technique is considered a promising administration method in terms of little pain to the patient and high dosage controllability. Nowadays iontophoresis is applied to administration of various drugs.

However, ion mobility based on the application of an electric field tends to decrease in inverse proportion to molecular weight of an ion. In particular, a higher-molecular-weight ion is more difficult to permeate through a biological interface (e.g., skin or mucous membrane), especially, stratum corneum. Hence, it has been said that a drug containing macromolecules such as protein or peptide molecules is hardly delivered through iontophoresis.

JP 10-510175 A discloses an iontophoresis device as shown in FIG. 6, as a device capable of delivering such a drug containing macromolecules.

As shown in FIG. 6, the device is structured such that a biological interface contact member (transferring means) 215 is interposed between a drug holding part (reservoir layer) 214 and a biological interface (skin) 240, the contact member having a substrate (supporting layer) on which a plurality of needles 252 to be inserted into the biological interface 240 are formed, and an electrical potential applied from an electrode 211 allows drug ions in the drug holding part 214 to pass through holes (flow path) 253 formed inside the needles 252 and migrate into the biological interface 240.

As described in JP 10-510175 A, the needles 252 are formed into lengths sufficient for the needle to pass completely or halfway through the stratum corneum 241 with substantially or absolutely no damage on an underlying biological interface surface 242. More specifically, the length ($L_N$) of the needle 252 is set to 1,000 µm (maximum) or shorter, particularly preferably, 1 µm to 500 µm. Hence, it is possible to eliminate pain in a patient at the time of delivering a drug. In addition, a porosity of the contact member 215 is set to 30% (maximum) or smaller. More specifically, the holes 253 or the needles 252 are formed in the contact member at the density of about 2,500 (holes or needles)/cm². The holes 253 each have a length ($L_K$) of 1 µm to 3,000 µm, particularly preferably, 10 µm to 1,000 µm, and the diameter of 0.03 µm to 300 µm, particularly preferably 0.1 µm to 100 µm. Hence, a drug purportedly can be delivered in sufficient amounts.

However, as a result of studies made by the inventors of the present invention, it was revealed that a delivery speed of a high-molecular-weight drug (drug containing macromolecules such as protein or peptide molecules) is far from sufficient even with the use of the device disclosed in JP 10-510175 A. In particular, the device faces a problem in that under such current or voltage conditions that cause no damage on the biological interface, it is impossible to deliver an effective amount of drug within a period acceptable as a drug delivery period.

BRIEF SUMMARY OF THE INVENTION

The present disclosure has been made in view of the above-described problem. An iontophoresis device capable of delivering to a living body, an ionizable drug (drug whose active ingredients dissociate into cations or anions when dissolved) of high-molecular-weight containing macromolecules such as protein or peptide molecules at high speed or with high efficiency is desirable.

It is also desirable to provide an iontophoresis device that may be capable of delivering a high-molecular-weight ionizable drug containing macromolecules such as protein or peptide molecules with high efficiency under lower current or voltage conditions.

It is still further desirable to provide an iontophoresis device that may be capable of delivering an ionizable drug with an efficiency or speed much higher than conventional iontophoresis devices including the device disclosed in JP 10-510175 A, irrespective of a molecular weight of the ionizable drug.

It is yet still further desirable to provide an iontophoresis device that may be capable of delivering an ionizable drug with high efficiency under low current or voltage conditions as compared with conventional iontophoresis devices including the device disclosed in JP 10-510175 A, irrespective of a molecular weight of the ionizable drug.

According to one embodiment, there is provided an iontophoresis device having a working electrode structure which comprises: a first electrode; a biological interface contact member including a substrate having a front surface and a rear surface, and a plurality of needles that protrude from the front surface of the substrate and can be inserted into a biological interface, the biological interface contact member allowing selective permeation of ions of a first polarity or conductivity type; and a drug holding part to be applied with an electrical potential or through the first electrode and holding a drug solution containing drug ions charged in the first polarity or conductivity type, the biological interface contact member being interposed between the first electrode and the biological interface.

That is, according to at least one embodiment, a first polarity or conductivity-type electrical potential or voltage is applied to the first electrode to deliver drug ions in the drug holding part into the living body through the needles inserted into the biological interface of the living body. Meanwhile, the biological interface contact member has a function of allowing selective permeation of the ions of the first polarity or conductivity type, whereby it is possible to prevent backflow of ions in the living body or at the surface of the biological interface of the living body (biological counter ion), which are of a second polarity or conductivity type opposite to that of the drug ions, to the drug holding part.

Thus, it is possible to avoid a situation in which most of the current supplied to the first electrode is consumed for migration of biological counter ion (particularly, biological counter ions having a low molecular weight, in other words, high mobility such as $Na^+$ or $Cl^-$) to the iontophoresis device. Therefore, a larger amount of current supplied to the first electrode can be used for migration of the drug ions to the living body, thereby considerably enhancing drug delivery efficiency or speed.

The iontophoresis device may attain the above operational effect and thus may make it possible to improve drug ion delivery efficiency or speed regardless of a molecular weight of a drug ion, or to further ease current or voltage conditions for the drug delivery, and deliver even drug ions of macromolecules such as protein or peptide molecules under lower current or voltage conditions at higher speed or higher efficiency.

Each of the needles may protrude from the substrate by a length sufficient for the needle to pass through all or most of a stratum corneum; which may be regarded as a main barrier against percutaneous delivery of a drug. A length of approximately 1,000 μm or shorter may be preferred, and approximately 1 μm to 300 μm may be particularly preferred.

The following first to fifth alternative embodiments may be particularly preferable.

According to the first alternative embodiment, in the iontophoresis device, the biological interface contact member has holes formed therein, the holes communicating between a tip end of each of the needles and the rear surface of the substrate, and at least a part of the holes are filled with an ion-exchange resin introduced with an ion-exchange group whose counter ion is the first polarity.

In this case, the first polarity or conductivity-type potential or voltage is applied to the first electrode to deliver drug ions in the drug holding part into the living body through the holes provided in the needles inserted into the biological interface of the living body. Meanwhile, the ion-exchange resin filled in the holes and introduced with an ion-exchange group whose counter ion is the first polarity conductivity type, prevents backflow of the biological counter ion to the drug holding part. Thus, the desired effects may be attained.

Here, any known ion-exchange resin can be used for the ion-exchange resin introduced with an ion-exchange group whose counter ion type is the first polarity or conductivity type. Examples thereof include an ion-exchange resin prepared by introducing a cation-exchange group (a group whose counter ion is cation) such as a sulfonic group, a carboxylic group, and a phosphonic group, or an anion-exchange group (a group whose counter ion is anion) such as primary to tertiary amino groups, a quaternary ammonium group, a pyridyl group, an imidazole group, a quaternary pyridinium group, or a quaternary imidazolium group into a polymer having a three-dimensional network structure such as hydrocarbon-based resins such as a polystyrene resin or acrylic acid resin or fluororesin-based resins having a perfluorocarbon skeleton.

The ion-exchange resin may be filled into the hole of the biological interface contact member by using any method, for example, by infiltrating or impregnating a monomer forming the hydrocarbon resin and blended with a crosslinking agent into the holes to cause a crosslinking reaction, or infiltrating or impregnating a powdery ion-exchange resin blended with a given binder polymer into the hole, and optionally curing the binder polymer.

The needles or the biological interface contact member of the first alternative embodiment can be formed of an organic material such as hard plastics or an inorganic material such as silicon by utilizing known methods such as lithography, molding, and laser irradiation.

The inner diameter of each of the holes formed in the biological interface contact member can be set, for example, to approximately 0.03 μm to 300 μm, although approximately 0.1 μm to 100 μm may be particularly preferable. The length of each of the holes from the rear surface of the substrate to the tip ends of the needles may, for example, be approximately 1 μm to 3,000 μm, although approximately 10 μm to 500 μm may be particularly preferable.

According to the second alternative embodiment, in the iontophoresis device, the biological interface contact member has holes formed therein, each of the holes communicating between a tip end of each of the needles and the rear surface of the substrate, and the biological interface contact member further includes a first ion-exchange membrane that is interposed between the drug holding part and the substrate and allows selective permeation of the ions of the first polarity or conductivity type.

In this case, the first polarity or conductivity-type electrical potential or voltage is applied to the first electrode, whereby drug ions in the drug holding part are delivered through the holes formed in the needles into the biological interface. Meanwhile, the biological counter ions cannot permeate through the first ion-exchange membrane and thus are accumulated in the holes of the biological interface contact member or a gap between the biological interface contact member and the first ion-exchange membrane. As a result, the migration of the biological counter ion is substantially blocked. Therefore, the drug ions may be delivered with delivery efficiency or speed comparable or approximate to that of the first alternative embodiment.

The needles or the skin contact member of the second alternative embodiment may have the same constitution as that of the first alternative embodiment.

Further, any ion-exchange membrane having a function of allowing selective permeation of ions of a first polarity or conductivity type and substantial blocking or suppressing the permeation of ions of a second polarity or conductivity type can be used as the first ion-exchange membrane of the second alternative. An ion-exchange membrane in which pores of a porous film are partially or completely filled with an ion-exchange resin introduced with an ion-exchange group whose counter ion is the first polarity or conductivity type, can preferably used as the first ion-exchange membrane of the second alternative.

The iontophoresis device according to the second alternative embodiment can be manufactured through a simple manufacturing process that interposes an ion-exchange membrane commercially available on the market etc. between the drug holding part and the substrate of the biological interface contact member. Thus an advantage in terms of a lower manufacturing cost can be obtained.

According to the third alternative embodiment, in the iontophoresis device, a plurality of columnar members made of an ion-exchange resin introduced with an ion-exchange group whose counter ion is of the first polarity or conductivity type, are embedded in the biological interface contact member, and the columnar members are each exposed to the rear surface of the substrate at one end and protrude by a predetermined length from the front surface of the substrate at the other end to form the needles insertable into the biological interface.

According to the third alternative embodiment, the columnar member made of an ion-exchange resin functions as both the needle insertable into the biological interface and the member that allows selective permeation of the ions of the first polarity or conductivity type, thereby attaining the operational effect.

That is, the drug ions in the drug holding part are delivered into the living body through the columnar members by the application of the first polarity or conductivity-type electrical potential or voltage to the first electrode. Meanwhile, the columnar members are formed of an ion-exchange resin introduced with an ion-exchange group whose counter ion is of the first polarity or conductivity type, whereby the biological counter ions are prevented from flowing back to the drug holding part through the columnar members. As a result, it may be possible to improve drug ion delivery efficiency or speed as in the first or second alternatives, or to further ease current or voltage conditions for the drug delivery, and deliver even drug ions containing macromolecules such as protein or peptide molecules under lower current or voltage conditions with higher efficiency or speed.

The resins described for the first alternative embodiment can be used as the ion-exchange resin introduced with the ion-exchange group whose counter ion is the first polarity or conductivity type, for forming the columnar members of the third mode. Examples of a method of molding the ion-exchange resin into a columnar shape include a method of molding hydrocarbon-based resins or a fluororesin forming the ion-exchange membrane into a linear shape through extrusion-molding, and then cutting the resultant into a predetermined size.

Note that the sectional shape of the columnar member may be arbitrarily set, for example, as a circle or rectangle. The length of the columnar member may, for example, be approximately 1 to 3,000 μm, or approximately 10 μm to 500 μm may be more preferred. The diameter of the columnar member may, for example, be approximately 0.03 to 300 μm, although approximately 0.1 μm to 100 μm may be more preferred. Further, the length of the needle made up of the columnar member (protrusion length of the columnar member from the front surface of the substrate) may be, for example, approximately 1,000 μm or smaller, although approximately 1 μm to 300 μm may be more preferred.

According to the fourth alternative embodiment, in the iontophoresis device, a plurality of multineedle members having a plurality of needle-like projections radially protruding therefrom, and made of an ion-exchange resin introduced with an ion-exchange group whose counter ion type is of the first polarity or conductivity type, are embedded in the biological interface contact member, and at least a part of a surface of each of the multineedle members is exposed to the rear surface of the substrate, and any one of the needle-like projections of the multineedle protrudes by a predetermined length from the front surface of the substrate to form the needle insertable into the biological interface.

According to the fourth alternative embodiment, as in the third alternative, the multineedle member made of an ion-exchange resin functions as both the needle insertable into the biological interface and the member that allows selective permeation of the ions of the first polarity or conductivity type, thereby attaining the operational effect.

That is, the drug ions in the drug holding part are delivered into the living body through the multineedle members by the application of the first polarity or conductivity-type electrical potential or voltage to the first electrode. Meanwhile, the multineedle members are formed of an ion-exchange resin introduced with an ion-exchange group whose counter ion is the first polarity or conductivity type, whereby the biological counter ion are prevented from flowing back to the drug holding part through the multineedle members. As a result, it may be possible to improve drug ion delivery efficiency or speed, or to further ease current or voltage conditions for the drug delivery, and deliver even drug ions containing macromolecules such as protein or peptide molecules under lower current or voltage conditions with higher efficiency or speed.

The resins described for the first alternative embodiment can be used as the ion-exchange resin introduced with the ion-exchange group whose counter ion is the first polarity or conductivity type, for forming the multineedle members of the fourth alternative.

Further, the needle-like projection of the multineedle of the fourth alternative may have a length of approximately 1,000 μm or shorter, where a length of approximately 1 μm to 300 μm, achievable through micromachining, for example, may be particularly preferred.

According to the fifth alternative embodiment, in the iontophoresis device, the biological interface contact member is formed of an ion-exchange membrane allowing selective permeation of the ions of the first polarity or conductivity type.

In this case, as in the third or fourth embodiments, drug ions in the drug holding part are delivered into the biological interface through the needles by the application of the first polarity or conductivity-type electrical potential or voltage to the first electrode. Meanwhile, the biological interface contact member is formed of the ion-exchange membrane allowing selective permeation of the ions of the first polarity or conductivity type, so the backflow of the biological counter ion into the drug holding part is blocked or suppressed, thereby possibly attaining the desired effects.

Here, the ion-exchange membrane of the fifth alternative embodiment may be made of the materials described for the second alternative.

The needles may be formed on the front surface of the ion-exchange membrane by press-molding the substrate constituting the ion-exchange membrane, for example.

In the iontophoresis device according to the third to fifth alternative embodiments, holes (also referred to as "recesses" in the descriptions for the embodiments) are preferably formed in the columnar members, the multineedle members, or the needles, the holes or recesses communicating with the opening at the rear surface of the substrate, whereby the drug ion delivery speed or efficiency may further be enhanced.

In the iontophoresis device, the working electrode structure may further include: a first electrolyte holding part for holding an electrolyte that is in contact with or proximate the first electrode; and a second ion-exchange membrane that is interposed between the first electrolyte holding part and the drug holding part and allows selective permeation of ions of a second polarity or conductivity type. With this arrangement, it is possible to avoid ion decomposition of the drug ions around the first electrode, migration of $H^+$ ions or $OH^-$ ions generated at the first electrode to the drug holding part, or resultant fluctuation in a pH value at the drug holding part and in turn, at the interface between the biological interface and the biological interface contact member, and inflammation caused on the biological interface contacting the biological interface contact member in some cases, and to achieve more stable, biologically compatible drug delivery.

The iontophoresis device may further include a nonworking electrode structure comprising: a second electrode; a second electrolyte holding part for holding an electrolyte that is in contact with the second electrode; a third ion-exchange membrane that is arranged on a front side of the second electrolyte holding part and allows selective permeation of the ions of the first polarity or conductivity type; a third electrolyte holding part that is arranged on a front side of the third ion-exchange membrane and holds an electrolyte; and a fourth ion-exchange membrane that is arranged on a front side of the third ion-exchange membrane and allows selective permeation of ions of a second polarity or conductivity type. With this arrangement, it is possible to avoid fluctuation in a pH value at the interface between the biological interface and the nonworking electrode structure, and inflammation caused on the biological interface contacting the nonworking electrode structure in some cases, and to achieve more stable, biologically compatible drug delivery.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

In the accompanying drawings.

DETAILED DESCRIPTION OF THE PREFERRED EMBODIMENTS

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with iontophoresis devices, ion exchange membranes, power sources, power supplies such as voltage and/or current regulators and/or controllers have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

Note that for ease of explanation, description is given of an embodiment of an iontophoresis device for delivering drugs whose active ingredients dissociate into positive drug ions (for example, lidocaine hydrochloride as an anesthetic, carnitine chloride as a remedy for gastrointestinal disorder, pancuronium bromide as muscle relaxants, and morphine hydrochloride as an anesthetic) by way of example. However, as regards an iontophoresis device for delivering drugs whose active ingredients dissociate into negative drug ions (for example, ascorbic acids as vitamins, and Lipid A used as a vaccine adjuvant), the polarity (positive or negative) of the electrodes of the power source and the ion-exchange group introduced to the ion-exchange membrane or the ion-exchange resin has only to be reversed. In addition, proteins and peptides are amphoteric electrolytes, which are dissociable into either cations or anions depending on pH of a drug solution. Thus, either one of the two is used depending on pH.

Figure 1:
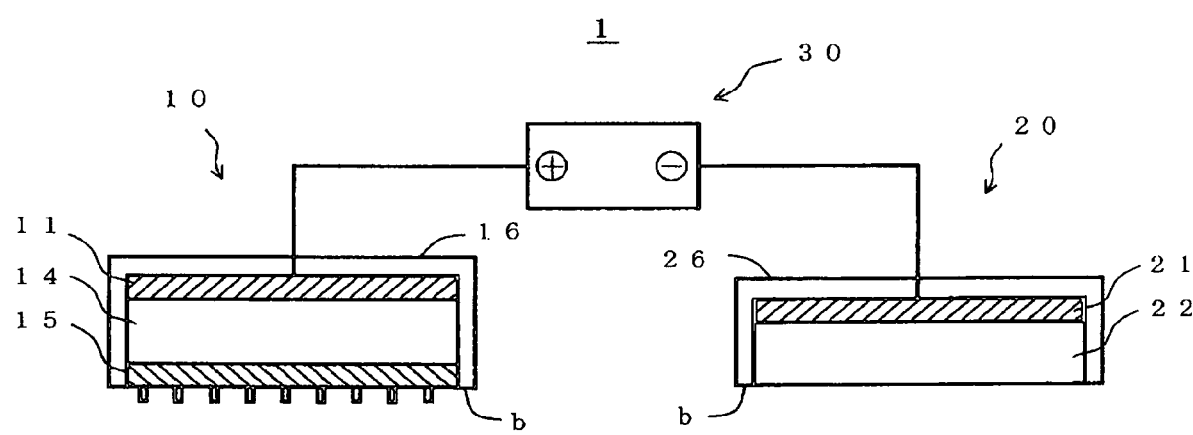
FIG. 1 is a schematic diagram showing an iontophoresis device according to one illustrated embodiment.

FIG. 1 is a schematic sectional diagram showing a basic structure of an iontophoresis device 1 according to one illustrated embodiment.

As illustrated in FIG. 1, the iontophoresis device 1 includes a working electrode structure 10, and a nonworking electrode structure 20, a power source 30 as main components (members).

The working electrode structure 10 includes: an electrode member 11 electrically coupleable with a positive electrode of the power source 30; a drug holding part 14 that holds a drug solution that is in contact with or proximate the electrode member 11 and applied with an electrical potential or voltage through the electrode member 11; a biological interface contact member 15 arranged on a front side of the drug holding part 14; and a cover or container 16 that accommodates those members.

Meanwhile, the nonworking electrode structure 20 includes: an electrode member 21 electrically coupleable with a negative electrode of the power source 30; an electrolyte holding part 22 that holds an electrolyte that is in contact with or proximate the electrode member 21 and applied with an electrical potential or voltage through the electrode member 21 and a cover or container 26 that accommodates those members.

As the electrode members 11 and 21, electrodes made of any conductive materials can be used with no particular limitations, and it may be particularly preferable to use an active electrode such as silver/silver halide coupled electrode, which can suppress generation of $H^+$ ions and $OH^-$ ions through electrolysis of water.

The drug holding part 14 holds an aqueous solution of a drug whose active ingredients dissociate into cations when dissolved (for example, proteins and peptides having positive charges in total in the solution, lidocaine, carnitine chloride, pancuronium bromide, and morphine hydrochloride) as a drug solution.

The electrolyte holding part 22 holds an electrolyte that enables current to flow. As the electrolyte, a phosphate buffered saline or physiological saline can be used. Alternatively, it is possible to use an electrolyte susceptible to oxidation or reduction as compared with an electrolytic reaction of water (i.e., oxidation at the positive electrode and reduction at the negative electrode), examples of which include: inorganic compounds such as ferrous sulfate and ferric sulfate; medicines such as an ascorbic acid (vitamin C) and sodium ascorbate; organic acids such as a lactic acid, an oxalic acid, a malic acid, a succinic acid, and fumaric acid and/or salts thereof; and mixtures thereof. The use thereof makes it possible to avoid fluctuation in pH value or gas generation due to the electrolytic reaction of water, and any resulting increase in ion conduction resistance.

The drug holding part 14 and the electrolyte holding part 22 may respectively retain the drug solution and electrolyte in a liquid form, or retain the drug solution and electrolyte in the form of being impregnated into a carrier made of any material having a water retentivity such as a fibrous sheet such as gauze or filter paper, or a polymer gel sheet made of an acrylic resin hydrogel (acrylic hydrogel) or segmented polyurethane-based gel. This facilitates, for example, handling thereof.

In this case, the degree of impregnation of the drug solution or electrolyte into the carrier is set to such a value as to ensure sufficient current supply and high transport number. The degree of impregnation of the drug solution is set to 20 to 60% for the drug holding part 14, whereby a transport number (drug delivering property) as high as 70 to 80% may be attained, for example.

Note that the degree of impregnation is represented by wt %, and derived from the expression of $100 \times (W-D)/D$ (%) where D represents a pre-impregnation (dry) weight and W represents a post-impregnation (wet) weight. The transport number indicates a ratio of current used for drug ion migration to total current supplied to the working electrode structure.

Figure 2A:
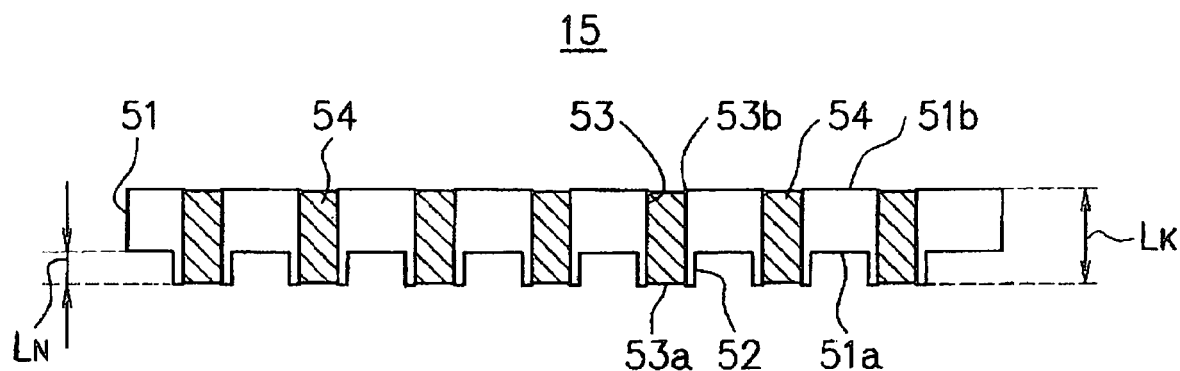
FIG. 2A is a cross-sectional view of a biological interface contact member used in the iontophoresis device according to one illustrated embodiment.

FIG. 2A is a conceptual explanatory diagram showing a detailed structure of the biological interface contact member 15 in the iontophoresis device 1.

As illustrated in FIG. 2A, the biological interface contact member 15 includes a substrate 51 having a front surface 51a and a rear surface 51b, and needles 52 each protruding from the front surface 51a and having a size, shape, and strength enough for the insertion into a biological interface (e.g., skin or mucous membrane). Formed in each needles 52 is a hole 53 communicating between an opening 53a at the tip end of the needle and an opening 53b at the rear surface of the substrate.

As a method of manufacturing the biological interface contact member 15, there are a variety of known manufacturing methods. For example, the biological interface contact member can be manufactured based on methods disclosed in U.S. Pat. No. 6,256,533 and JP 2005-503194 A, both of which are incorporated herein by reference, to mold organic materials such as plastics or etch inorganic materials such as silicon.

Here, the length ($L_N$) of each of the needles 52 of the biological interface contact member 15 may be approximately 1,000 μm or shorter, while approximately 1 μm to 300 μm may be preferred. Hence, it is possible to relieve pain in a patient at the time of delivering a drug. In addition, the length ($L_K$) of each of the holes 53 extending from the opening 53a at the tip end of the needle to the opening 53b at the rear surface of the substrate may be approximately 1 to 3,000 μm, while approximately 10 μm to 500 μm may be preferred. The inner diameter of each of the holes 53 may be approximately 0.03 μm to 300 μm, while approximately 0.1 μm to 100 μm may be preferred. Hence, it may be possible to secure a flow path large enough for smooth delivery of drug ions. The needles 52 or holes 53 of the biological interface contact member 15 may be formed at the density of several to 5,000 (holes or needles)/cm², for example.

Figure 6:
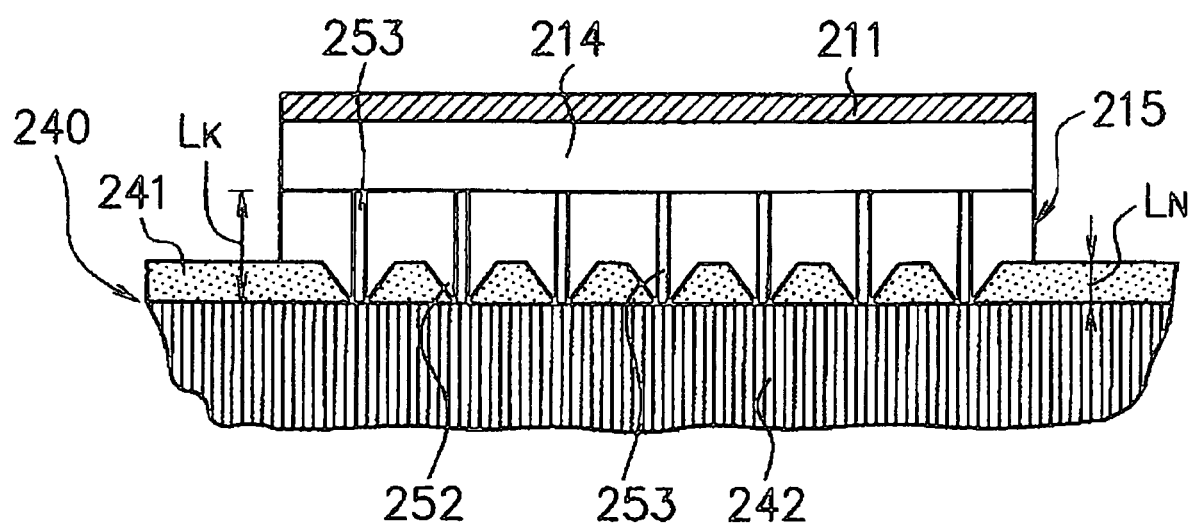
FIG. 6 is a cross-sectional view that illustrates an example of a conventional iontophoresis device.

Note that each of the needles 52 and/or the holes 53 may have any sectional shape such as a circular shape, an elliptical shape, or a rectangular shape. Besides, they may be formed into such a shape that has a uniform sectional area in a longitudinal direction of the needle 52 as shown in FIG. 2A or a tapered shape as shown in FIG. 6, which facilitates insertion into the biological interface.

In addition, a cation-exchange resin (ion-exchange resin introduced with an ion-exchange group whose counter ion is cation) 54 fills the holes 53 of the biological interface contact member 15.

As the above cation-exchange resin 54, usable is a resin prepared by introducing a cation-exchange group such as a sulfonic group, a carboxylic group, or a phosphonic group into a polymer substrate having a three-dimensional network structure such as hydrocarbon-based resins such as a polystyrene resin or acrylic acid resin or fluororesin-based resins having a perfluorocarbon skeleton.

The holes 53 may be filled with the cation-exchange resin 54 by using any method, for example, by impregnating the tip ends of the needles 52 or the entire biological interface contact member 15 with a solution prepared by mixing a crosslinking monomer forming the polymer substrate such as styrene-divinylbenzene or chloromethylstyrene-divinylbenzene with a polymerization initiator; by charging the solution from the rear surface 51b of the substrate 51 using a spatula member so that the solution is infiltrated or impregnated into the holes 53, followed by polymerization and then introduction of the cation-exchange group; or by infiltrating or impregnating into the holes 53, a binder polymer such as a phenol resin or methyl methacrylate into which a fine powder of a cation-exchange resin is dispersed, in place of the above solution in the above way, and then curing the resultant binder polymer.

The cation-exchange resin 54 can be filled to the full length of the holes 53 as shown in FIG. 2A, or may be partially filled, for example, filled into only a portion of the holes 53 around the openings 53a at the tip ends of the needles 52.

Figure 2B:
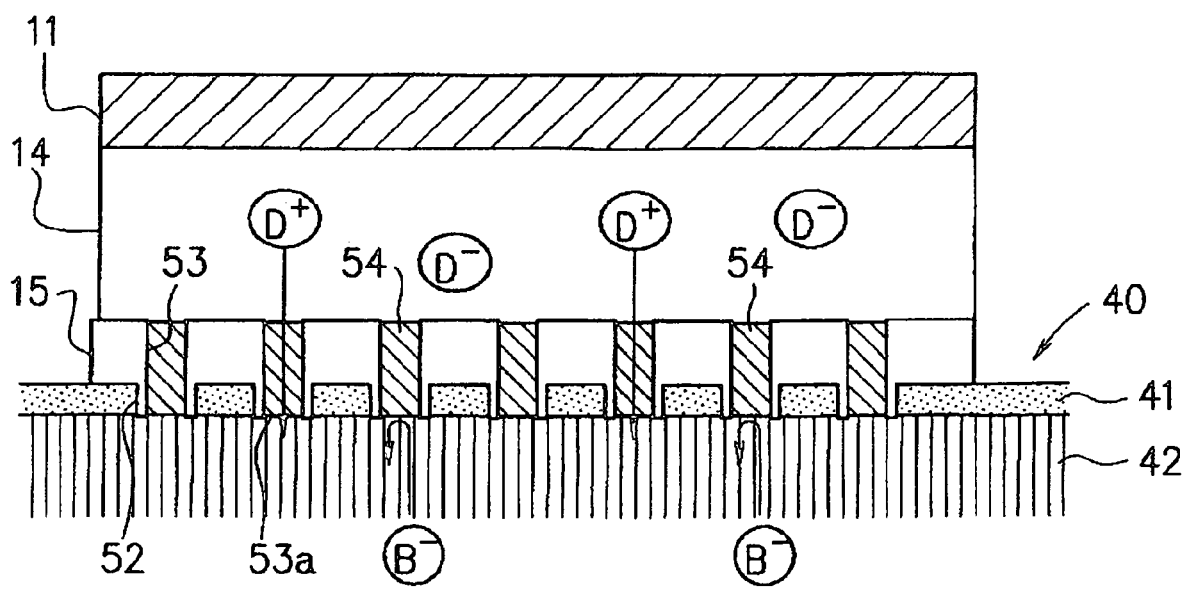
FIG. 2B is a schematic diagram that illustrates how ions migrate in the iontophoresis device.

FIG. 2B schematically illustrates how ions migrate in the drug holding part 14 and a biological interface 40 when the voltage is applied through the electrode member 11 and electrode member 21 with the biological interface contact member 15 brought into contact with the biological interface 40. In FIG. 2B, $D^+$ represents a positively charged drug ion, $D^-$ represents a counter ion thereof (drug counter ion), and $B^-$ represents a negative ion in the living body or at the surface of the biological interface 40. In addition, reference numerals 41 and 42 denote a stratum corneum covering the biological interface surface and a subcutaneous tissue underlying the stratum corneum, respectively.

The drug ions $D^+$ in the drug holding part 14 are driven through the application of a positive electrical potential or voltage to the electrode member 11 to migrate to the biological interface 40 through the holes 53. At this time, the drug ions $D^+$ can permeate through the cation-exchange resin 54 filled in the holes 53 because of its positive polarity.

In addition, the inserted needles 52 penetrate the stratum corneum 41 which is normally a barrier against the migration of the drug ions $D^+$, so the drug ions $D^+$ having reached the opening 53a can migrate into the subcutaneous tissue 42 without being blocked by the stratum corneum 41. Note that it may be most preferable that all the needles 52 completely penetrate the stratum corneum 41 like the illustrated example, but the drug delivery may be performed while all or some of the needles 52 are partway (e.g., halfway) inserted into the stratum corneum 41. In this case as well, the drug delivery efficiency can be improved according as the thickness of the stratum corneum 41 from the opening 53a to the subcutaneous tissue 42 is reduced.

In contrast, the biological counter ions $B^-$ present in the living body or at the surface of the biological interface are attracted to the drug holding part 14 side through the application of a positive electrical potential or voltage to the electrode member 11, but the migration of the biological counter ion $B^-$ is completely blocked or suppressed to an allowable level owing to the cation-exchange resin 54 filled in the holes 53.

Accordingly, a ratio of current consumed for the migration of the biological counter ion $B^-$ to the drug holding part 14 to total current supplied to the electrode member 11 may be reduced or minimized substantially to zero, which increases a ratio of current consumable for the migration of the drug ions $D^+$ to the living body to the total current. As a result, delivery speed and efficiency of the drug ions $D^+$ may improve, or the drug ions $D^+$ may be delivered efficiency under lower current or voltage conditions.

Note that the ion mobility tends to reduce in reverse proportion to molecular weight. Hence, when the cation-exchange resin 54 does not fill the hole 53, the biological counter ion B⁻ consumes more current upon migration to the drug holding part 14 in the case of delivering the drug ion D⁺ having a higher molecular weight. Therefore, an effect of improving the drug ion delivery speed and efficiency may be greatly enhanced in the case of using a drug ion of a higher molecular weight, which was hardly delivered with the conventional iontophoresis device.

A battery, a constant voltage generator, a constant current source, a constant voltage/current source, and the like can be used as the power source 30 in the iontophoresis device. A constant current source operable under stable voltage conditions that enable arbitrary current adjustment in a range of approximately 0.01 to 1.0 mA/cm² may be preferred, while approximately 0.01 to 0.5 mA/cm² may be more preferred, more specifically, voltage conditions of approximately 50 V or lower, for example 30V or lower may be particularly preferred.

In the above iontophoresis device, a liner may be attached to the front side of the biological interface contact member 15 and/or the electrolyte holding part 22 for the purpose of preventing the drug holding part 14 or the electrolyte holding part 22 from drying or preventing foreign substances from mixing into the drug holding part 14 or the electrolyte holding part 22, or an adhesive layer for improving adhesion between the working electrode structure 10 and/or the nonworking electrode structure 20, and the biological interface may be laminated on a bottom "b" of the cover or container 16 and/or the cover or container 26.

FIG. 3A to 3G illustrate alternative structures for the biological interface contact members 15a to 15g, each of which can replace the biological interface contact member 15 (FIG. 1).

Figure 3A:
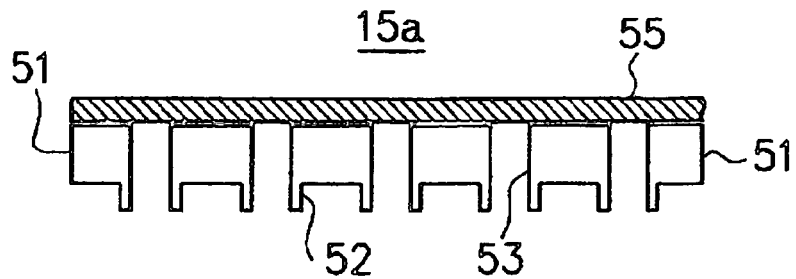
FIGS. 3A to 3G each illustrate respective alternative embodiments of the biological interface contact member.

The biological interface contact member 15a of FIG. 3A has the same or similar substrate 51, the needles 52, and the holes 53 as in the biological interface contact member 15. Instead of filling the cation-exchange resin 54 into the holes 53, a cation-exchange membrane (i.e., ion-exchange membrane allowing selective permeation of cations) 55 is provided on the rear side of the substrate 51 and the front side of the drug holding part 14.

With an iontophoresis device using the above biological interface contact member 15a, the drug ions D⁺ permeate through the cation-exchange membrane 55 and the holes 53, and are then delivered into the living body through the opening at the tip end of the needle 52 due to the electrical potential or voltage applied to the electrode member 11 as in the iontophoresis device 1.

In contrast, the cation-exchange membrane 55 blocks or suppresses the migration of the biological counter ion B⁻ to the drug holding part 14, so the biological counter ions B⁻ are accumulated in the hole 53 and substantially inhibited from migrating.

Accordingly, a larger amount of supplied current can be used for migration of the drug ions D⁺ into the living body, possibly improving the delivery speed and efficiency of the drug ions D⁺ or enabling the drug delivery under lower current or voltage conditions.

Note that as the cation-exchange membrane 55 used herein, any cation-exchange membrane having a function of allowing selective permeation of cations can be used, examples of which include NEOSEPTA CM-1, CM-2, CMX, CMS, and CMB (available from Tokuyama Co., Ltd.). A cation-exchange membrane prepared by completely or partially filling a cation-exchange resin into pores of a porous film made of a polyolefin resin, vinylchloride-based resins, fluororesin-based resins, a polyamide resin, a polyimide resin, or the like may be particularly preferred. The cation-exchange resin may be filled by, for example, impregnating into the pores of the porous film, a solution prepared by mixing a crosslinking monomer such as styrene-divinylbenzene or chloromethylstyrene-divinylbenzene with a polymerization initiator, followed by polymerization and then introduction of cation-exchange groups such as a sulfonic group, a carboxylic group, and a phosphonic group into the polymer.

In addition, it may be preferable to bond the cation-exchange membrane 55 and the substrate 51 at the interface by an appropriate method such as bonding by use of an adhesive or ultrasonic bonding. This overcomes a problem in that a gap is left at the interface to increase the migration amount of the biological counter ion B⁻ or bubbles are generated to lower the conductivity.

Figure 3B:
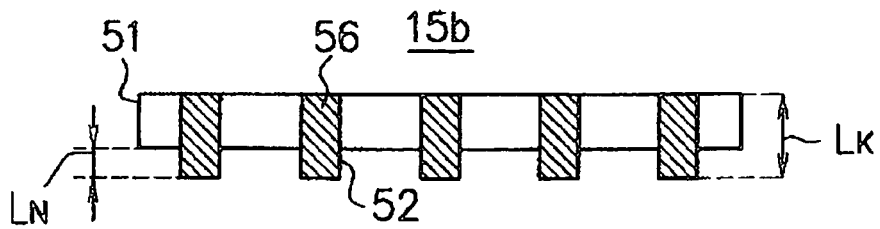

The biological interface contact member 15b of FIG. 3B includes: the substrate 51 as in the biological interface contact member 15; and a number of columnar members 52 embedded into the substrate 51 and made of a cation-exchange resin. Each columnar member 56 is exposed to the rear surface of the substrate 51 at one end, and protrudes by a predetermined length from the front surface of the substrate 51 at the other end to constitute the needle 52.

With an iontophoresis device using the above biological interface contact member 15b, the drug ions D⁺ permeate through the columnar member 56 to be delivered into the living body through the application of a positive electric potential or voltage to the electrode member 11 similarly to the iontophoresis device 1. Meanwhile, the cation-exchange resin forming the columnar member 56 blocks or suppresses the migration of the biological counter ion B⁻ to the drug holding part 14, so a larger amount of supplied current can be used for migration of the drug ions D⁺ into the living body, possibly improving the delivery speed or efficiency of the drug ions D⁺ or enabling the drug delivery under lower current or voltage conditions.

Those described for the cation-exchange resin 54 of the biological interface contact member 15 can be used as the cation-exchange resin forming the columnar member 56. Besides, the member can be formed into a columnar shape through machining such as micromachining or through extrusion-molding of hydrocarbon-based resins or a fluororesin forming the cation-exchange resin into a linear shape, followed by cutting into a predetermined size with the cation-exchange groups being introduced before or after the cutting.

Regarding the size of the columnar member 56, the length ($L_K$) of the columnar member 56 may, for example, be approximately 1 to 3,000 μm, while approximately 10 μm to 500 μm may be preferred. If the columnar member 56 is circular in section, its diameter may be, for example, approximately 0.03 to 300 μm, while approximately 0.1 μm to 100 μm may be preferred. Further, in embedding the columnar member into the substrate 51, the protrusion length ($L_N$) from the front surface of the substrate 51 may be, for example, approximately 1,000 μm or smaller, while approximately 1 μm to 300 μm may be more preferred.

Note that the sectional shape of the columnar member 56 is not limited to a circle but may be any shape such as an ellipse or rectangle. In addition, the member can be tapered towards its tip end to facilitate the insertion to the biological interface.

Figure 3C:
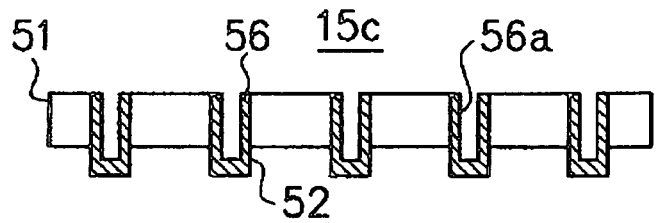

The biological interface contact member 15c of FIG. 3C has the same or similar structure as the biological interface contact member 15b except that recesses 56a are defined in the columnar member 56 to open at the rear surface of the substrate 51.

Accordingly, with an iontophoresis device using the biological interface contact member 15c, the drug ions D⁺ are delivered in the same or similar way as in the case of using the biological interface contact member 15b. However, the drug solution from the drug holding part 14 can be infiltrated into the recesses 56a, making it possible to deliver drug ions with higher efficiency than the case of using the biological interface contact member 15b.

Note that the recesses 56a can be formed through machining such as micromachining of the columnar member 56 manufactured by the above method.

Figure 3D:
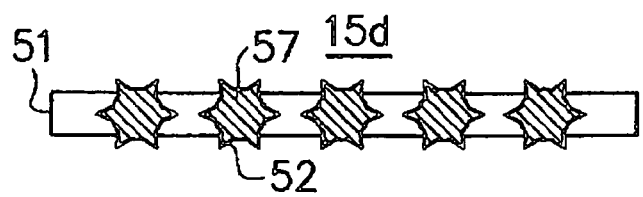

The biological interface contact member 15d of FIG. 3D includes: the substrate 51 as in the biological interface contact member 15; and a number of multineedle members 57 embedded into the substrate 51 and made of a cation-exchange resin. As shown in FIG. 3D, the multineedle members 57 each have plural needle-like projections that radially protrude. Any of the needle-like projections protrude from the front surface of the substrate 51 and serve as the needles 52. Further, the multineedle members 57 are embedded into the substrate 51 in such a form that at least a part thereof is exposed to the rear surface of the substrate 51.

A resin similar to that for the columnar members 56 can be used as the cation-exchange resin of the multineedle members 57. The multineedle members 57 can be shaped through micromachining or the like.

With an iontophoresis device using the above biological interface contact member 15d, the drug ions $D^+$ permeate through the multineedle members 57, and are then delivered into the living body due to the positive electrical potential or voltage applied to the electrode member 11 as in the iontophoresis device 1. Meanwhile, the cation-exchange resin forming the multineedle members 57 substantially blocks or suppresses the migration of the biological counter ion $B^-$ to the drug holding part 14. Accordingly, a larger amount of supplied current may be used for migration of the drug ions $D^+$ into the living body, possibly improving the delivery speed or efficiency of the drug ions $D^+$ or enabling the drug delivery under lower current or voltage conditions.

Note that the biological interface contact member 15d is advantageous in that a manufacturing process can be simplified as compared with the biological interface contact member 15b because the multineedle members 57 having an appropriate number of needle-like projections with an appropriate length enables any of the needle-like projections to protrude to the front surface 51a of the substrate 51 even when embedded into the substrate 51 regardless of an embedding direction (orientation) of the multineedle members, and enables at least a part of the multineedle members 57 to be exposed to the rear surface 51b of the substrate 51.

Figure 3E:
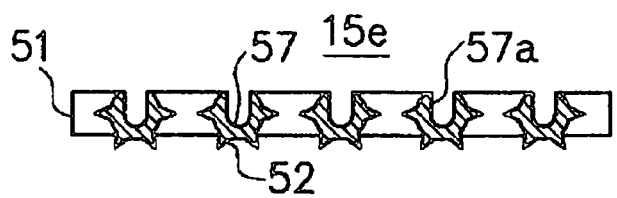

The biological interface contact member 15e of FIG. 3E has the same structure as the biological interface contact member 15d except that recesses 57a are defined in the multineedle members 57 to open on the rear surface 51b of the substrate 51.

Accordingly, in the iontophoresis device using the biological interface contact member 15e, the drug ion delivery is carried out in a way similar to that using the biological interface contact member 15d. However, the drug solution from the drug holding part 14 can be infiltrated into the recesses 57a, whereby the drug ion may be delivered with higher efficiency than that in the case of using the skin contact member 15d.

The recesses 57a can be formed through micromachining or the like.

Figure 3F:
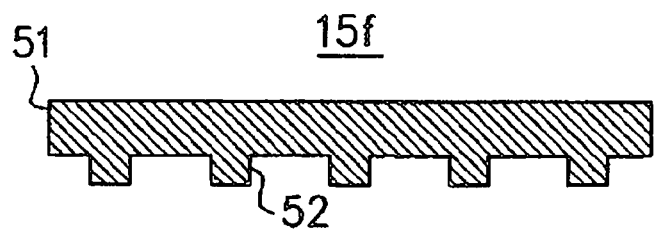

The biological interface contact member 15f of FIG. 3F includes: the substrate 51; and the needles 52 protruding from the front surface of the substrate 51, and the skin contact member 15f is made up of a cation-exchange membrane in its entirety.

Figure 4A:
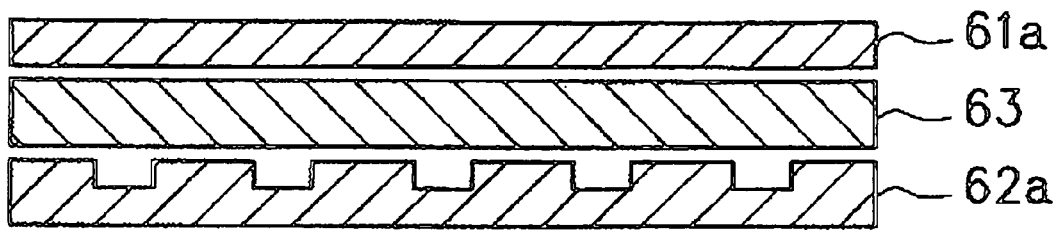
FIGS. 4A and 4B are cross-sectional view that illustrate an example of a manufacturing method for a biological interface contact member.

The above biological interface contact member 15f can be molded by using molds 61a and 62a as shown in FIG. 4A, for example.

More specifically, a porous film 63 made of a thermoplastic resin such as a polyolefin resin, vinylchloride-based resins, fluororesin-based resins, a polyamide resin, or a polyimide resin is press-molded between the molds 61a and 62a. After that, a cation-exchange resin is filled into the pores of the porous film 63 based on the same method as that for the cation-exchange membrane 55, or the porous film 63 whose pores are previously filled with the cation-exchange resin is press-molded between the molds 61a and 62a to thereby form the biological interface contact member 15f.

Alternatively, the above biological interface contact member 15f can be produced by molding a binder polymer such as polyethylene, polystyrene, a phenol resin, or methyl methacrylate into which a fine powder of a cation-exchange resin is dispersed, between the molds 61a and 62a into a membrane.

With an iontophoresis device using the biological interface contact member 15f, the drug ions $D^+$ permeate through the biological interface contact member 15f, and are then delivered into the living body from the tip ends of the needles 52 due to the positive electrical potential or voltage applied to the electrode member 11 as in the iontophoresis device 1. Meanwhile, the biological interface contact member 15f as a cation-exchange membrane substantially blocks or suppresses the migration of the biological counter ion $B^-$ to the drug holding part 14. Accordingly, a larger amount of supplied current may be used for migration of the drug ions $D^+$ into the living body, possibly improving the delivery speed or efficiency of the drug ions $D^+$ or enabling the drug delivery under lower current or voltage conditions.

In addition, with this iontophoresis device, the drug ions $D^+$ can migrate into the living body from other portions than the needles 52 of the substrate 51 in contact with the biological interface 40 albeit migration by way of the stratum corneum 41. Thus, especially in the case where a drug ion having a relatively low molecular weight is used, or a drug ion of which a significant quantity can be delivered through the stratum corneum 41 is used, the drug delivery speed or efficiency may further be enhanced.

Figure 3G:
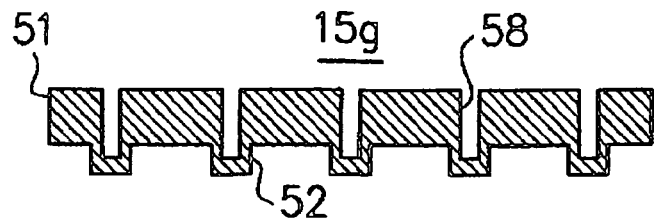

The biological interface contact member 15g of FIG. 3G has the same or similar structure as the biological interface contact member 15f except that recesses 58 extend from the rear surface of the substrate 51 to the inside of the needles 52 in the biological interface contact member 15g.

Figure 4B:
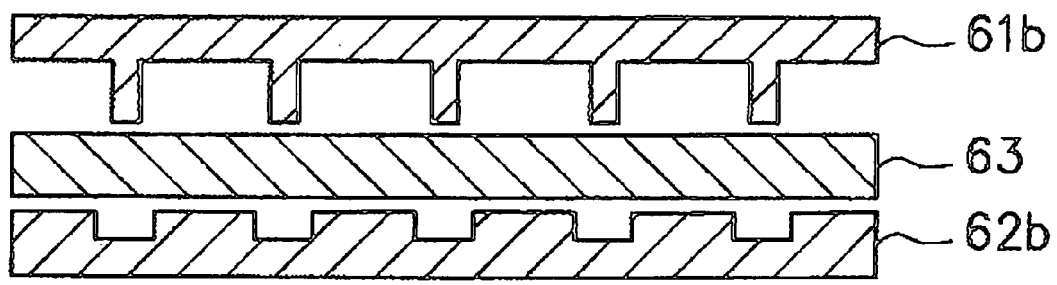

The biological interface contact member 15g can be molded using molds 61b and 62b as shown in FIG. 4B by the similar ways as those for the biological interface contact member 15f.

An iontophoresis device using the biological interface contact member 15g delivers drug ions in a similar way to that in the case the biological interface contact member 15f is used. However, the drug solution from the drug holding part 14 can be infiltrated into the recesses 58, whereby the drug ion can be delivered with a higher efficiency than that in the case of using the biological interface contact member 15g.

Figure 5:
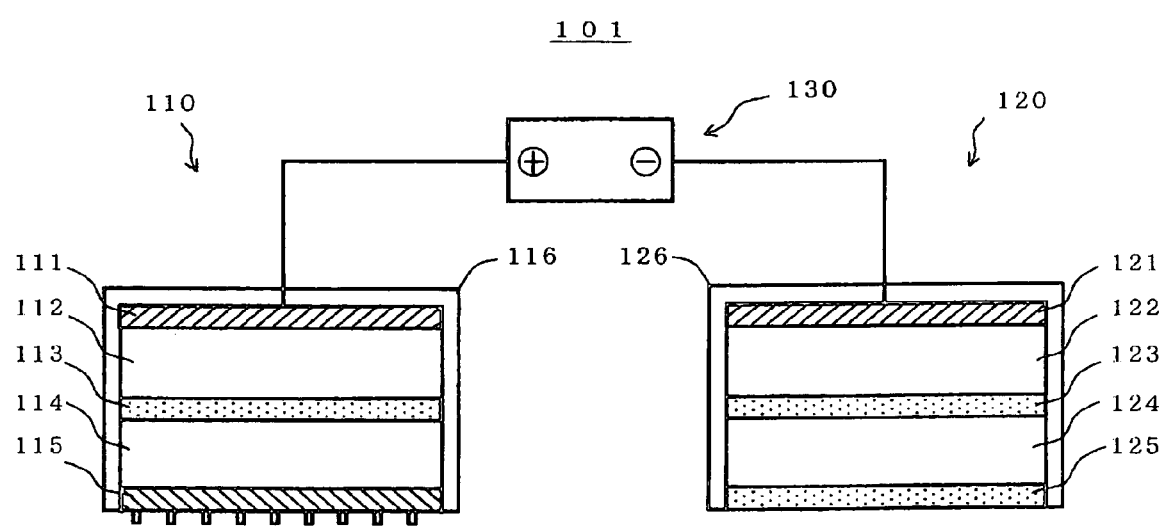
FIG. 5 is a schematic diagram showing an iontophoresis device according to another illustrated embodiment.

FIG. 5 illustrates a structure of an iontophoresis device 101 according to another embodiment.

An iontophoresis device 101 includes a working electrode structure 110, a nonworking electrode structure 120, and a power source 130 like the iontophoresis device 1.

The working electrode structure 110 includes: an electrode member 111 electrically coupleable with a positive electrode of the power source 130; an electrolyte holding part 112 that holds an electrolyte that is in contact with or proximate the electrode member 111 and is subjected to an electrical potential or voltage through the electrode member 111; an anion-exchange membrane 113 arranged on a front side of the electrolyte holding part 112; a drug holding part 114 that is placed on a front side of the anion-exchange membrane 113 and holds a drug solution that is subjected to the potential or voltage from the electrode member 111 through the electrolyte holding part 112 and the anion-exchange membrane 113; a biological interface contact member 115 arranged on a front side of the drug holding part 114; and a cover or container 116 that accommodates those members.

Meanwhile, the nonworking electrode structure 120 includes: an electrode member 121 electrically coupleable with a negative electrode of the power source 130; an electrolyte holding part 122 that holds an electrolyte that is in contact with or proximate the electrode member 121 and is subjected to the potential or voltage through the electrode member 121; a cation-exchange membrane 123 arranged on a front side of the electrolyte holding part 132; an electrolyte holding part 124 that is placed on a front side of the cation-exchange membrane 123 and holds an electrolyte that is subjected to a potential or voltage from the electrode member 121 through the electrolyte holding part 122 and the cation-exchange membrane 123; an anion-exchange membrane 125 arranged on a front side of the electrolyte holding part 124; and a cover or container 126 that accommodates those members.

Here, the electrode members 111 and 121, the drug holding part 114, and the electrolyte holding parts 112, 122, and 124 have the same structures as the electrode members 11 and 21, the drug holding part 14, and the electrolyte holding part 22, respectively, and membranes similar to the above-described membranes for the cation-exchange membrane 55 can be used for the cation-exchange membrane 123.

As the anion-exchange membranes 113 and 125, for example, any anion-exchange membrane having a function of allowing selective permeation of anions can be used, examples of which include NEOSEPTA AM-1, AM-3, AMX, AHA, ACH, and ACS (available from Tokuyama Co., Ltd.). An anion-exchange membrane prepared by filling an anion-exchange resin into pores of a porous film similar to that for the cation-exchange membrane 55 may be particularly preferred. In this case, the anion-exchange resin may be filled by, for example, impregnating into the pores of the porous film, a solution prepared by mixing a crosslinking monomer such as styrene-divinylbenzene or chloromethylstyrene-divinylbenzene with a polymerization initiator, followed by polymerization and then introduction of anion-exchange groups to the polymer.

Further, usable as the biological interface contact member 115 are members similar to the biological interface contact member 15 or the biological interface contact members 15a to 15f.

The iontophoresis device 101 may achieve an operational effect equivalent to the above effect of the iontophoresis device 1 or the devices replacing the biological interface contact member 15 of the iontophoresis device 1 with any of the biological interface contact members 15a to 15f, and may further attain the following additional operational effect.

That is, the anion-exchange membrane 113 or cation-exchange membrane 123 functions to substantially block or suppress the migration of $H^+$ ions or $OH^-$ ions generated at the electrode members 111 and 121 due to the voltage application from the electrode members 111 and 121 to the drug holding part 114 and the electrolyte holding part 124. Thus, it is possible to suppress fluctuation in pH value in the drug holding part 114 and the electrolyte holding part 124 and in turn, at the contact surfaces of the working electrode structure 110 and the nonworking electrode structure 120 to the biological interface. As a result, a damage to the biological interface may be reduced to enhance a biocompatibility of the drug delivery.

Further, as discussed above, the migration of $H^+$ or $OH^-$ ions to the drug holding part 114 and the electrolyte holding part 124 is substantially blocked or suppressed, whereby a carbon electrode as an inactive electrode can be used for the electrode members 111 and 121 in place of the active electrode such as a silver/silver halide coupled electrode. Consequently, it is possible to attain an iontophoresis device free of such a problem that metal ions eluting from the electrode migrate into the living body.

Further, the drug holding part 114 is separated from the electrode member 111 by the anion-exchange membrane 113, which may eliminate a problem by preventing or inhibiting ion decomposition of drug ions around the electrode member 111 which might otherwise generate a hazardous substance.

The present invention has been described so far based on several embodiments. The present invention is not limited to those embodiments but allows any addition, change, and deletion of the components in the embodiments within the scope of claims.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. An iontophoresis device having a working electrode structure, said working electrode structure comprising:
   a first electrode;
   a biological interface contact member including a substrate having a front surface and a rear surface, and a plurality of needles that protrude from the front surface of the substrate and which can be inserted into a biological interface, the needles including an ion exchange material that allows selective permeation of ions of a first polarity and substantially prevents permeation of ions of a second polarity, opposite to the first polarity; and
   a drug holding part to hold a drug solution containing drug ions of the first polarity, the drug holding part interposed between the first electrode and the biological interface contact member, wherein the drug ions are driven through the ion exchange material of the needles from the drug holding part in response to an electrical potential applied via the first electrode.

2. The iontophoresis device according to claim 1, wherein the biological interface contact member is formed of an ion-exchange membrane allowing selective permeation of the ions of the first polarity.

3. The iontophoresis device according to claim 2, wherein holes are formed in the biological interface contact member, each of the holes extending from an inner portion of each of the needles to an opening at the rear surface of the substrate.

4. The iontophoresis device according to claim 2, wherein the needles and the biological interface contact member are a unitary structure.

5. The iontophoresis device according to claim 1, wherein the plurality of needles are a plurality of micro-needles.

6. The iontophoresis device according to claim 5, wherein the needles are formed of the ion-exchange material.

7. The iontophoresis device according to claim 1, wherein:
each of the needles having at least one hole formed therein, each of the holes communicating with a respective tip end of the needle; and
the ion exchange material includes an ion-exchange resin that fills at least a part of each of the holes, the ion-exchange resin having an ion-exchange group whose counter ion is of the first polarity.

8. The iontophoresis device according to claim 1, wherein:
the plurality of needles are made of an ion-exchange resin introduced with an ion-exchange group whose counter ion is of the first polarity.

9. The iontophoresis device according to claim 1, wherein the working electrode structure further includes:
a first electrolyte holding part for holding an electrolyte that is in contact with the first electrode; and
a second ion-exchange membrane that is interposed between the first electrolyte holding part and the drug holding part and allows selective permeation of ions of a second polarity, opposite to the first polarity.

10. The iontophoresis device according to claim 1, further comprising a nonworking electrode structure including:
a second electrode;
a second electrolyte holding part for holding an electrolyte that is in contact with the second electrode;
a third ion-exchange membrane that is arranged on a front side of the second electrolyte holding part and allows selective permeation of the ions of the first polarity;
a third electrolyte holding part that is arranged on a front side of the third ion-exchange membrane and holds an electrolyte; and
a fourth ion-exchange membrane that is arranged on a front side of the third ion-exchange membrane and allows selective permeation of ions of a second polarity.

* * * * *